US007970199B2

(12) United States Patent
Yoshida et al.

(10) Patent No.: US 7,970,199 B2
(45) Date of Patent: Jun. 28, 2011

(54) METHOD AND APPARATUS FOR DETECTING DEFECT ON A SURFACE OF A SPECIMEN

(75) Inventors: Minoru Yoshida, Yokohama (JP); Yoshimasa Oshima, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1033 days.

(21) Appl. No.: 11/757,458

(22) Filed: Jun. 4, 2007

(65) Prior Publication Data

US 2007/0285670 A1    Dec. 13, 2007

(30) Foreign Application Priority Data

Jun. 5, 2006   (JP) .................................. 2006-155892

(51) Int. Cl.
*G06K 9/00* (2006.01)
*G01B 11/02* (2006.01)
(52) U.S. Cl. ...................................... 382/145; 356/497
(58) Field of Classification Search .................. 382/145; 356/497
See application file for complete search history.

(56) References Cited

U.S. PATENT DOCUMENTS

| 4,978,219 A * | 12/1990 | Bessho .......................... 356/489 |
| 5,061,071 A * | 10/1991 | Fujita et al. .................... 356/489 |
| 5,076,693 A * | 12/1991 | Teramoto ....................... 356/489 |
| 5,430,548 A * | 7/1995 | Hiroi et al. ..................... 356/394 |
| 6,552,803 B1 * | 4/2003 | Wang et al. .................... 356/503 |
| 6,762,831 B2 * | 7/2004 | Shibata et al. ............. 356/237.2 |
| 6,806,959 B2 * | 10/2004 | Tukker .......................... 356/484 |
| 6,992,779 B2 * | 1/2006 | Ueki ............................. 356/512 |
| 7,042,556 B1 * | 5/2006 | Sun .............................. 356/4.07 |
| 7,274,468 B2 * | 9/2007 | Hill et al. ...................... 356/520 |
| 7,423,766 B1 * | 9/2008 | Li .................................. 356/521 |
| 2005/0057756 A1 * | 3/2005 | Fang-Yen et al. ............. 356/497 |
| 2006/0192975 A1 * | 8/2006 | Sato et al. ..................... 356/497 |

FOREIGN PATENT DOCUMENTS

JP    2000-121318    4/2000

* cited by examiner

*Primary Examiner* — Wenpeng Chen
(74) *Attorney, Agent, or Firm* — Antonelli, Terry, Stout & Kraus, LLP.

(57) ABSTRACT

A surface inspection apparatus is provided based on an optical interference scheme using a wide-band laser light source, such as diode laser, for an interferometer. In the apparatus, a diode laser with a large spectrum width having a short coherence length is used as an emitted light source; modulation optical elements for performing modulation with slightly different frequencies, and optical path length varying optical elements for adjusting the optical path length are located in each of two optical paths between a branching optical element and a combining optical element; and the above-mentioned optical path length varying optical elements are adjusted, while measuring an interference intensity, so as to maximize the interference intensity.

18 Claims, 8 Drawing Sheets

FLAT SPECIMEN

UNEVEN SPECIMEN

FIG. 6A
FIG. 6B
FIG. 6C
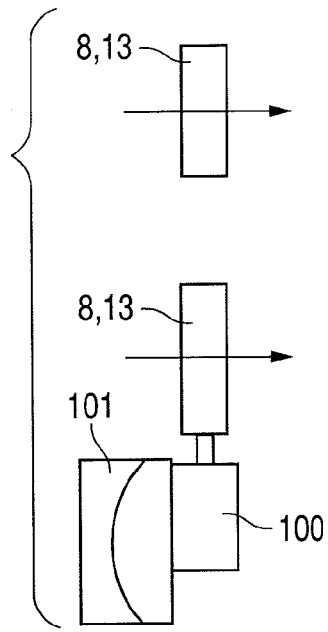
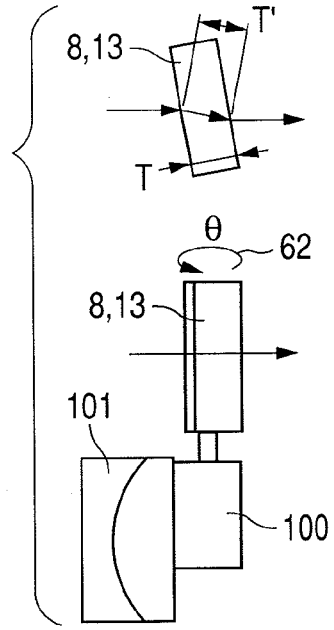
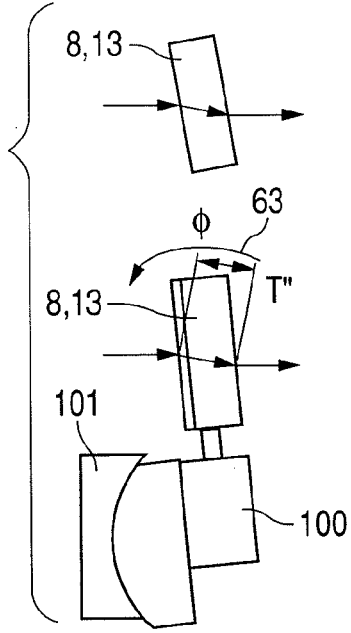
FIG. 7
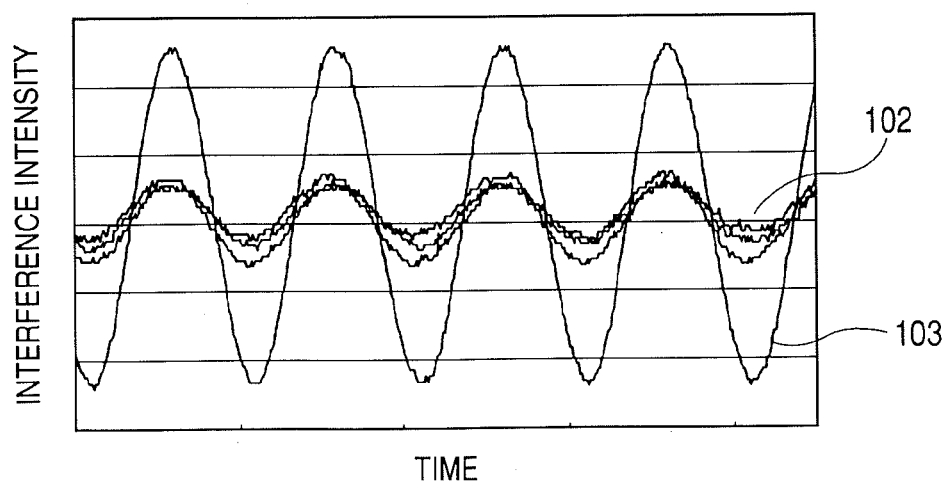

FIG. 10
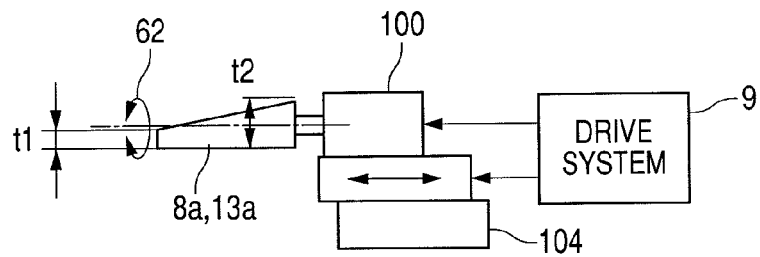
FIG. 11A          FIG. 11B          FIG. 11C
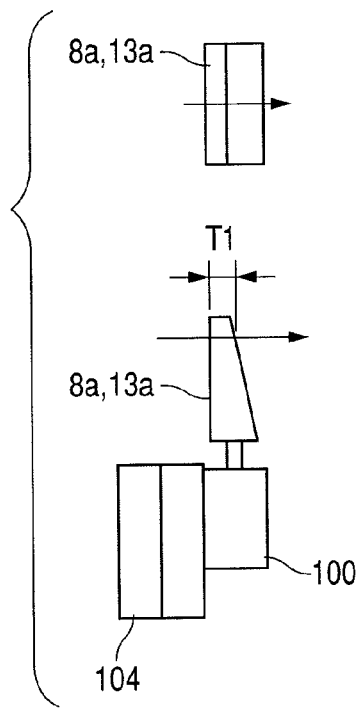 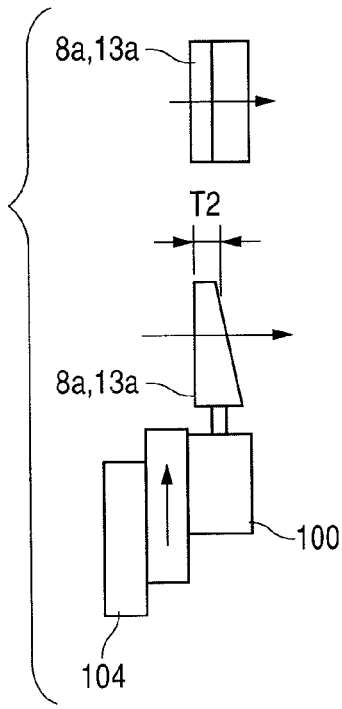 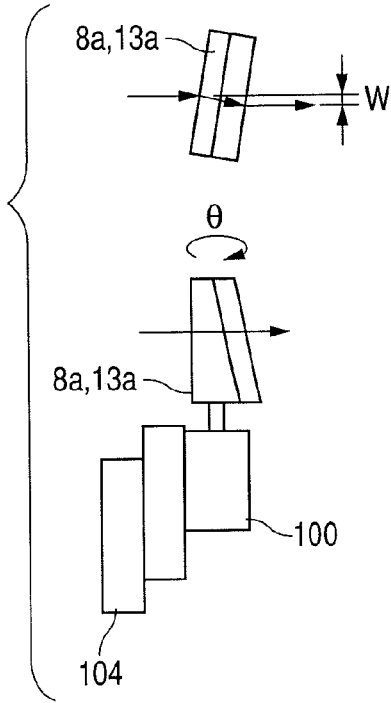
FIG. 12
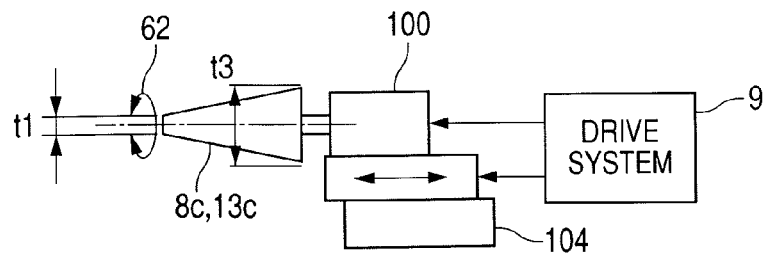

METHOD AND APPARATUS FOR DETECTING DEFECT ON A SURFACE OF A SPECIMEN

BACKGROUND OF THE INVENTION

1. Field of the Invention

The present invention relates to a surface inspection apparatus for detecting defect on a surface of a magnetic disk substrate. More particularly, the present invention relates to a surface inspection method and apparatus for measuring the shape of a defect through phase detection.

2. Description of the Related Art

A disk substrate with evaporated magnetic substance is used as a magnetic recording medium for a hard disk drive. Data is magnetically written and read by magnetizing the disk substrate by use of a magnetic head. In recent years, with an increase in the recording density of hard disk drive, the space (hereinafter referred to as flying height) between a recording head (hereinafter referred to as head) and the disk substrate is becoming much narrower, i.e., from several tens of nanometers to several nanometers. Therefore, if minute concavo-convex defect exists on the disk substrate, the head comes in contact with the disk substrate which may cause failure of the hard disk drive.

Therefore, it is important to detect the above-mentioned defect on a substrate before evaporating the magnetic substance to prevent a defective product from being transferred to subsequent processes. This minute concavo-convex defect is possibly a crystal defect buried in the disk substrate material, a residual abrasive particle or a fine flaw (scratch or the like) produced in polishing process performed to improve the flatness of the disk substrate, or a foreign material which adheres to the surface in washing or drying process. Foreign substances adhering to the surface can be eliminated and prevented through re-washing, purification of atmosphere, or other appropriate measures. However, since crystal defect, a scratch, etc. are unrepairable, a product with such defect will be handled as a defective one. Therefore, in order to ensure high yield and high reliability of hard disk drive, early elimination of disk substrates having such defect is essential. Furthermore, since the above-mentioned defect may occur because of a certain reason even after magnetic substance has been evaporated, it is possible to improve the reliability of hard disk drive by similarly detecting defect and eliminating defective products.

Conventionally, measurement of surface roughness based on an AFM (atomic force microscope) is commonly used as a method for measuring minute concavo-convex defect. In AFM-based measurement, the throughput is remarkably slow and therefore it is not easy to perform entire surface inspection. Furthermore, this method has some drawbacks: for example, a measurement probe is a consumable; measurement reproducibility fluctuates because of a worn probe, etc.

Therefore, there is a method adapting interference of light. As shown in JP-A-2000-121318, there is a method for measuring the height of defect from variation of phase by performing the steps of branching a laser beam, modulating branched light beams with different frequencies, irradiating reference and measurement surfaces with the laser beams, and allowing respective reflected light beams to interfere on a light-sensitive element. In accordance with above-mentioned JP-A-2000-121318, a laser beam with a lighting wavelength of 532 nm is used, an interference signal with a frequency of 10 MHz is outputted, and the change of an optical path length of the measurement surface is converted into a phase, thus enabling measurement of the height of defective from the phase difference.

By the way, as a laser beam used for an interference optical system described in above-mentioned JP-A-2000-121318, a highly coherent narrow-band laser having a narrow spectrum width (such as gas laser and diode-pumped solid state laser) is used. The coherence length is several tens of millimeters to several meters, which causes no problem on interference in terms of the optical path length of the reference and measurement surfaces. FIG. 9 shows a spectrum distribution of a narrow-band laser with a wavelength of 532 nm which is a diode-pumped solid state laser. Thus, a narrow-band laser has a spectrum of 1 nm or less, generally giving a coherence length ranging from several tens of millimeters to several meters.

However, since the shape of target defect is becoming more and more minute as mentioned above, the improvement in the detection sensitivity is required. In the case of the interference-phase measurement scheme, since the period of an interference signal is a half of the laser wavelength, the detection sensitivity is determined by the laser wavelength. Therefore, to improve the detection sensitivity, it is necessary to shorten the wavelength of a laser light source. To shorten the wavelength of the laser light source, highly advanced adjustment is required using a crystal according to each wavelength to obtain a plurality of high order harmonics. As the wavelength is shortened, therefore, the structure of the laser light source becomes more complicated resulting in remarkably high price. For this reason, there arises a subject of increased price of a surface inspection apparatus.

However, technology for shortening the wavelength has progressed even in the case of diode laser making it easier to obtain a low-price high-power light source. However, diode laser has a larger spectrum width than the above-mentioned diode-pumped solid state laser. In particular, diode laser with a shortened wavelength has a subject of a larger spectrum width than diode laser with a long wavelength. Thus, since the coherence length becomes remarkably shorter with increasing spectrum width, diode laser is not suitable as a light source for the above-mentioned interference optical system.

On the other hand, there is a method for narrowing a band of diode laser having a large spectrum width using a diffraction grating. With this method, a specific wavelength is taken out from the diffraction grating and therefore the output is remarkably reduced and at the same time the arrangement of the diffraction grating is delicate. There arises a subject of aging as well as a subject that laser beam cannot be taken out because of vibratory effect on the diode laser light source. Furthermore, since the configuration of the diode laser light source may become complicated, there arises a subject of high price.

SUMMARY OF THE INVENTION

The present invention is concerned with a surface inspection apparatus based on an optical interference system using a wide-band laser light source, such as diode laser, for an interferometer, wherein diode laser with a large spectrum width having a short coherence length is used as an illuminating light source; modulation optical elements 5 and 10 for performing modulation with slightly different frequencies, and optical path length varying optical elements 8 and 13 for adjusting the optical path length are located in each of two optical paths between a branching optical element 4 and a combining optical element 15; and the above-mentioned optical path length varying optical elements 8 and 13 are adjusted, while measuring an interference intensity, so as to maximize the interference intensity.

The present invention provides a method and a low-price apparatus for surface inspection which make it possible to measure the shape of minute concavo-convex defect (including surface roughness) on a surface of a disk substrate having a tendency to reducing surface roughness, based on the interference-phase measurement scheme using a diode laser light source with a large spectrum width having a very short coherence length of several millimeters.

Specifically, the present invention is concerned with a surface inspection apparatus for measuring the surface shape of a measurement surface by causing interference of reflected lights on the reference and measurement surfaces. The surface inspection apparatus comprises a laser light source; a branching optical element which branches a laser beam emitted from the laser light source; a first modulation optical element which is located in a first optical path branched by the branching optical element and which modulates the above-mentioned first branch laser beam with a first frequency, and a first optical path length varying optical element which can adjust the optical path length; a second modulation optical element which is located in a second optical path branched by the branching optical element and which modulates the above-mentioned second branch laser beam with a second frequency different from the first frequency, and a second optical path length varying optical element which can adjust the optical path length; a combining optical element which combines a first modulation laser beam modulated with a first frequency obtained from the above-mentioned first optical path and a second modulation laser beam modulated with a second frequency obtained from the above-mentioned second optical path; a measurement unit for measuring the interference intensity after the combination, which is obtained from the combining optical element; a drive control system which performs adjustment and control of at least the above-mentioned first or second optical path length varying optical element based on the interference intensity measured by the measurement unit; an interference measurement optical system which branches again the interference light after the combination, interference light being obtained from the above-mentioned combining optical element, and which irradiates the above-mentioned reference surface with one branch laser beam, irradiates the above-mentioned measurement surface with the other branch laser beam, recombines reflected light beams from the above-mentioned reference and measurement surfaces, and detects an interference intensity of the recombined laser beam as an interference signal; and a signal processing unit for detecting a phase difference of the interference signal detected by the interference measurement optical system, and calculating a surface shape of the above-mentioned measurement surface according to the phase difference of the detected interference signal.

Furthermore, the above-mentioned measurement means of the present invention is constructed so that the interference intensity of the laser beam recombined by the above-mentioned interference measurement optical system is measured as an interference intensity after the combination, which is obtained from the above-mentioned combining optical element.

Furthermore, the present invention is concerned with a surface inspection method for measuring a surface shape of a measurement surface by causing interference of reflected light beams from the reference and measurement surfaces. The surface inspection method includes an interference measurement process, signal processing process, and optical path length adjustment process. The interference measurement process includes the steps of: branching a laser beam emitted from a laser light source using a branching optical element; modulating respectively the above-mentioned first and second branch optical beams with first and second frequencies which are different from each other using a first and second modulation optical elements in the first and second branch optical paths; combining the first and second modulated modulation laser beams using a combining optical element; branching again the interference light after the combination, which is obtained through the combination by an interference measurement optical system; irradiating the above-mentioned reference surface with one branch laser beam; irradiating the above-mentioned measurement surface with the other branch laser beam; recombining reflected light beams from the above-mentioned reference surface and the above-mentioned measurement surface; and detecting an interference intensity of the recombined laser beam as an interference signal. The signal processing process includes the steps of detecting a phase difference of an interference signal detected in the interference measurement process; and calculating a surface shape of the above-mentioned measurement surface according to the detected phase difference of the interference signal. The optical path length adjustment process includes the steps of locating first and second optical path length varying optical elements which can adjust optical path length respectively in the above-mentioned first and second optical paths; measuring the above-mentioned combined or recombined interference intensity using a measurement means in the interference measurement process; and adjusting at least the above-mentioned first or second optical path length varying optical element based on the measured interference intensity.

Furthermore, the above-mentioned laser light source of the present invention is a diode laser light source which emits a laser beam having a wavelength of about 410 nm or less, a wavelength of up to far-ultraviolet radiation.

In accordance with the present invention, it is possible to measure the shape of crystal defect, a residual abrasive particle, a fine flaw (scratch or the like), a foreign material, and other minute concavo-convex defects (including surface roughness) on a surface of a disk substrate having a tendency to decreasing surface roughness due to improved surface recording density, decreased size of hard disk drive, etc. based on the interference-phase measurement scheme using a diode laser light source with a large spectrum width having a very short coherence length of several millimeters, thus realizing a method and a low-price simply constructed apparatus for surface inspection.

These and other objects, features and advantages of the invention will be apparent from the following more particular description of preferred embodiments of the invention, as illustrated in the accompanying drawings.

BRIEF DESCRIPTION OF THE DRAWINGS

FIG. 4 is a diagram showing an interference waveform signal which is combined by a combining optical element and detected by a photoelectric conversion sensor or the like.

FIG. 6A is a plan view (top) and a front view (bottom) showing an optical path length varying element (optical path length adjustment plate) before adjustment; FIG. 6B is a plan view (top) and a front view (bottom) showing the optical path length varying element in the state where the optical path length varies based on refraction of light by movement in a rotational direction 62 with respect to an optical axis; and FIG. 6C is a plan view (top) and a front view (bottom) showing the optical path length varying element in the state where an optical path length varies based on refraction of light by movement of the optical path length varying element (optical path length adjustment plate) in a turn direction 63 with respect to the optical axis.

FIG. 7 is a diagram showing a condition where amplitude of interference increases through adjustment of an optical path length varying element (optical path length adjustment plate).

FIG. 10 is a diagram showing an optical path length varying element (optical path length adjustment plate) according to another embodiment of the present embodiment.

FIG. 11A is a diagram showing the optical path length varying element (optical path length adjustment plate) before adjustment; FIG. 11B is a diagram showing the optical path length varying element in the state where the optical path length varies based on refraction of light by movement of the optical path length varying element in a direction orthogonal to the optical axis; and FIG. 11C is a diagram showing the optical path length varying element (optical path length adjustment plate) in the state where the optical path length varies based on refraction of light by movement of the optical path length varying element (optical path length adjustment plate) in a turn direction 63 with respect to the optical axis.

FIG. 12 is a diagram showing an optical path length varying element (optical path length adjustment plate) according to another embodiment of the present embodiment.

DESCRIPTION OF THE PREFERRED EMBODIMENTS

Embodiments of a surface inspection method and apparatus of the present invention for measuring the shape of minute concavo-convex defect on a surface of a substrate, such as a disk substrate, based on the interference-phase measurement scheme will be described below with reference to the accompanying drawings.

First Embodiment

Figure 2:
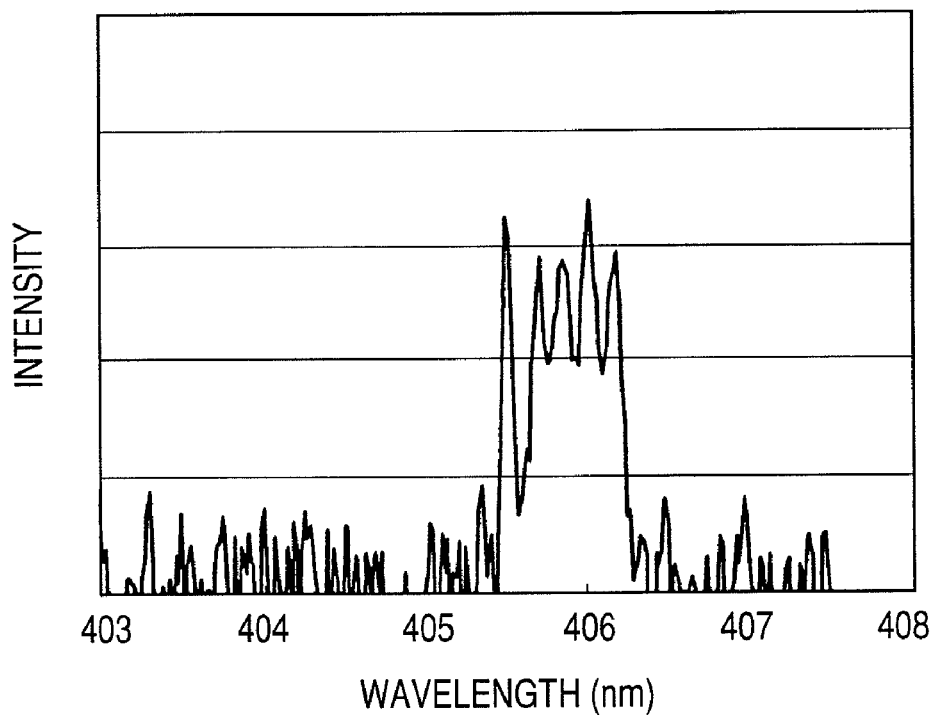
FIG. 2 is a diagram showing a wide-band spectrum width of a diode laser.
Figure 9:
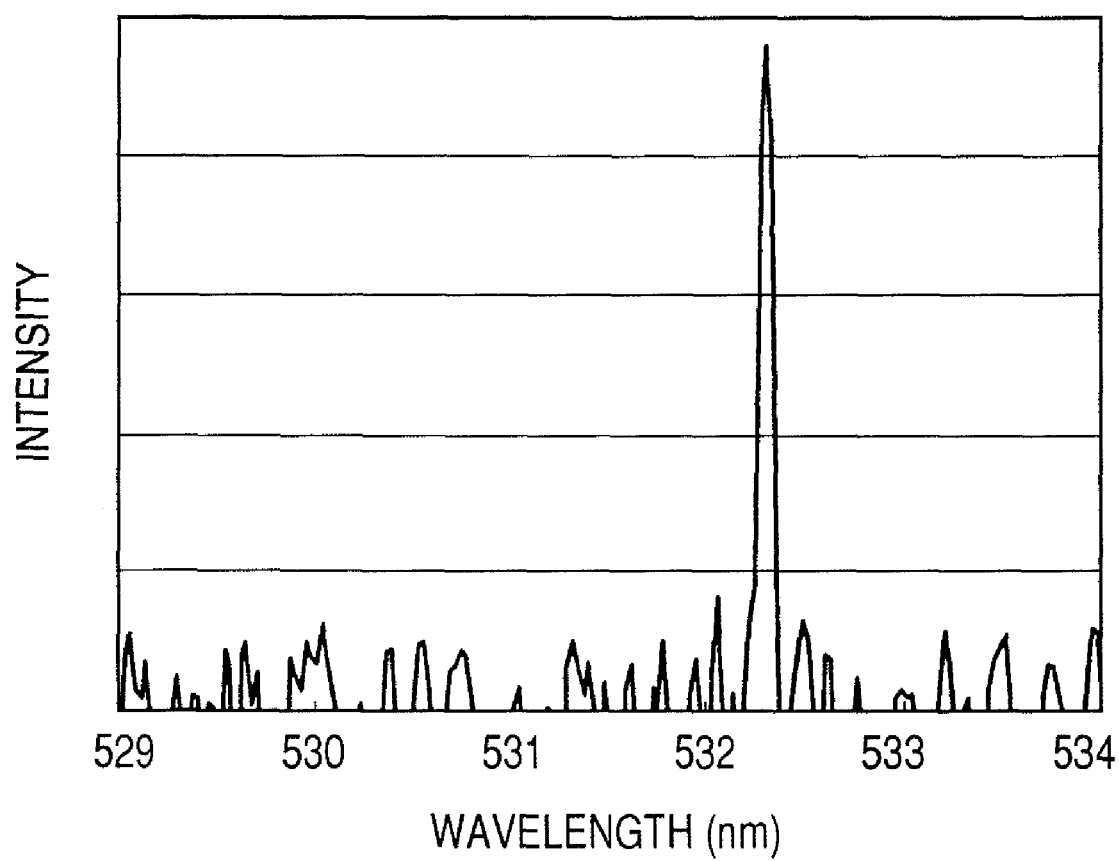
FIG. 9 is a diagram showing a spectrum distribution of narrow-band laser with a wavelength of 532 nm, which is diode-pumped solid state laser.

A first embodiment of a surface inspection method and apparatus of the present invention will be described below with reference to the accompanying drawings. FIG. 2 shows an example of a wide-band spectrum distribution of diode laser of the present invention. Thus, in the case of diode laser, the wavelength is shorter than that of diode-pumped solid state laser (with a wavelength of 532 nm) having a narrow-band spectrum distribution as shown in FIG. 9. However, the spectrum width is several nanometers, generally making it possible to obtain a coherence length of only several millimeters. The present invention is concerned with a surface inspection method and apparatus for measuring the shape of minute concavo-convex defect (including surface roughness) on a surface of a substrate, such as a disk substrate, based on the interference-phase measurement scheme using such wide-band laser.

Figure 1:
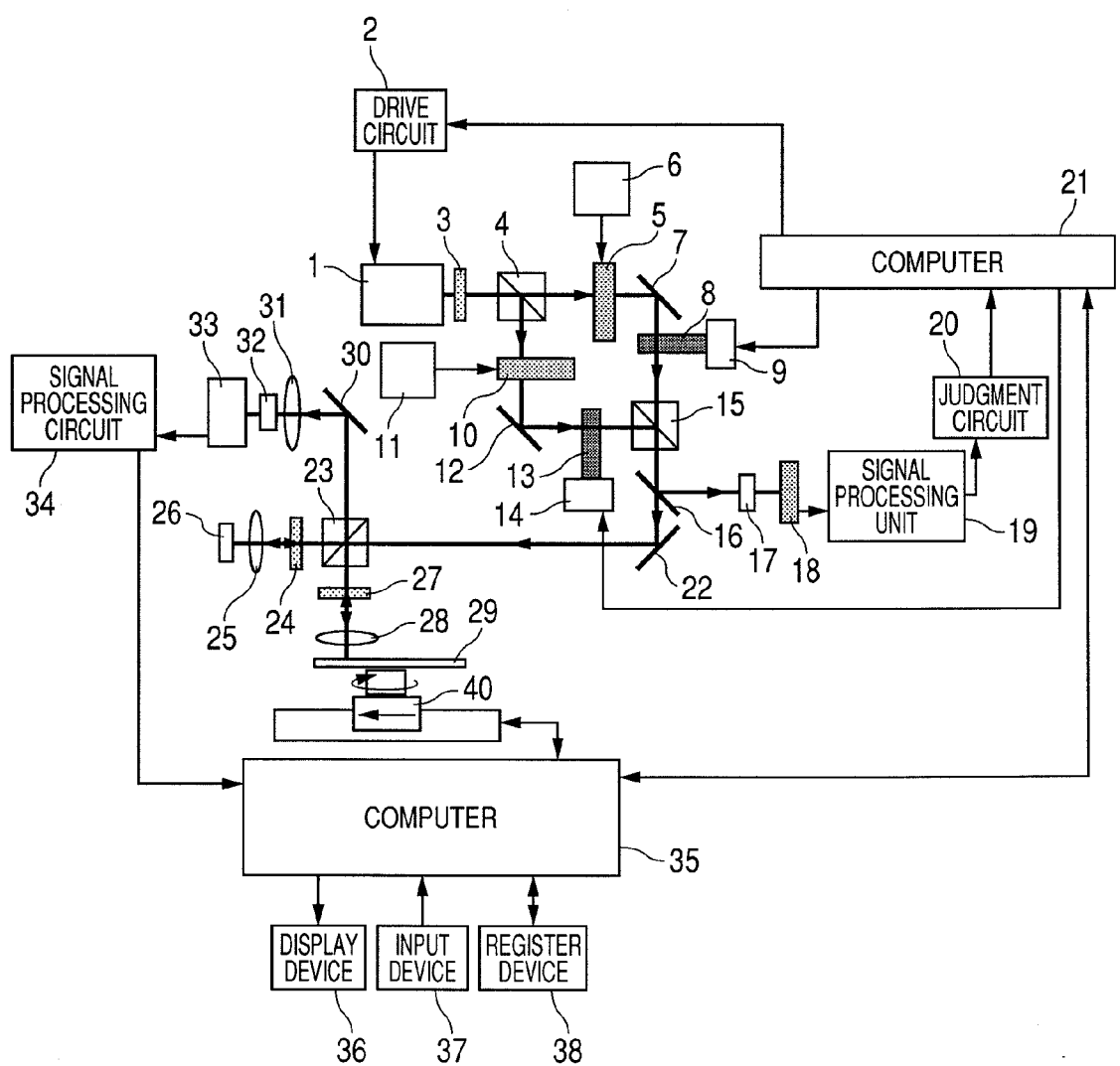
FIG. 1 is a front view showing an outline configuration of a surface inspection apparatus according to a first embodiment of the present invention.

A first embodiment of a surface inspection apparatus of the present invention will be described below. FIG. 1 shows an overall configuration of a first embodiment of a surface inspection apparatus of the present invention. For a low-price diode laser light source 1 which emits a wide-band laser beam having a spectrum width of several nanometers, temperature control and current control are performed by a drive circuit 2 based on a method (not shown). In order to measure the shape of minute concavo-convex defect on a surface of a specimen, such as a disk substrate, having a tendency to decreasing surface roughness due to improved surface recording density, decreased size of hard disk drive, etc., it would be possible that the wavelength of a laser beam emitted from the diode laser light source 1 is about 410 nm or less even for visible light or that the beam is ultraviolet or far-ultraviolet radiation. Furthermore, a laser beam emitted from the diode laser light source 1 has linear polarization. Furthermore, the polarization direction of the laser beam is inclined by 45 degrees by a λ/2 plate 3. Then, the laser beam is branched into two using a polarized beam splitter (PBS) (A) 4 which is a first branch optical element. Since polarization is inclined by 45 degrees, the beam is equally branched into reflected light and transmitted light by PBS (A) 4. An S-polarized laser beam which penetrated through the PBS (A) 4 penetrates through an acousto-optic modulator (AOM) (A) 5 which is a modulation optical element, and then is modulated to a predetermined frequency fa by an acoustic element drive circuit (A) 6.

Figure 3:
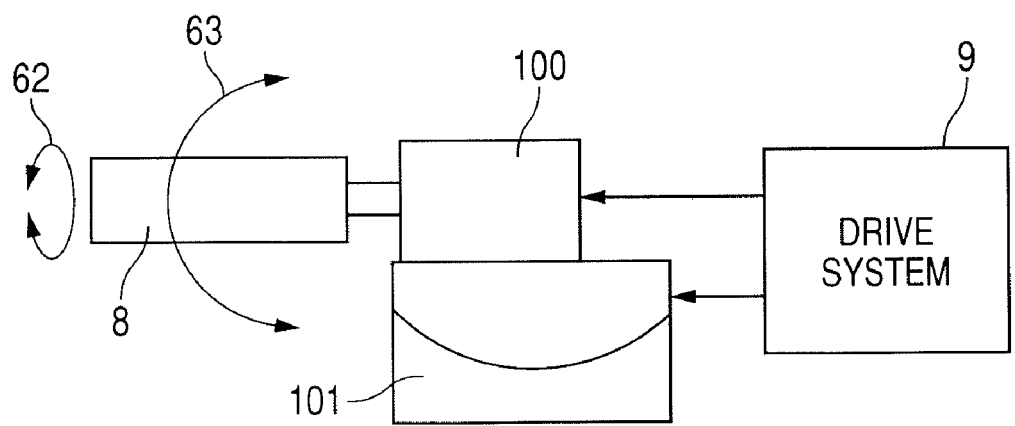
FIG. 3 is a diagram showing a method for driving an optical path length adjustment plate.

The laser beam modulated by the acousto-optic modulator (A) 5 reflects off a mirror 7 and then penetrates through an optical path length varying element (optical path length adjustment plate) (A) 8. The optical path length adjustment plate (A) 8 is fixed to a rotary mechanism 100 allowing movement in the rotational direction 63, as shown in FIG. 3. Furthermore, the rotary mechanism 100 is fixed to a turn mechanism 101, allowing movement in the turn direction 63. The rotary mechanism 100 and the turn mechanism 101 can be controlled by a drive system 9.

The P-polarized laser beam reflected by the PBS (A) 4 penetrates through an acousto-optic modulator (B) 10 and then is modulated to a predetermined frequency fb by an acoustic element drive circuit (B) 11 which is a modulation optical element. The laser beam modulated by the acousto-optic modulator (B) 10 reflects off a mirror 12 and then penetrates through an optical path length varying element (optical path length adjustment plate) (B) 13. Like the optical path length adjustment plate (A) 8, the optical path length adjustment plate (B) 13 can be controlled by a drive system 14 both in the rotational direction and the turn direction, as illustrated in FIG. 3.

The S-polarized reflected light and the P-polarized transmitted light branched by the PBS (A) 4 are respectively reflected and transmitted by a PBS (B) 15 which is a first combination optical element, resulting in combined coaxial lights (beams). Two optical path lengths from the PBS (A) 4 to the PBS (B) 15 are set to almost the same distance.

A laser lights (beams) combined by the PBS (B) 15 penetrates through a transparent glass plate 16 inclined by 45 degrees with respect to the optical axis and then reflects off a mirror 22. Here, on the surface of the transparent glass plate 16, slightly reflected coaxially-combined laser beams can be taken out. Since this slightly laser lights is formed with S-polarized light and P-polarized light, these laser lights are not interfered under such polarized lights. Therefore, these laser lights are irradiated to a photoelectric conversion sensor 18 so as to take place interference of respective laser lights by inclining the polarization plane at 45 degrees with using a polarizing plate 17.

Figure 4:
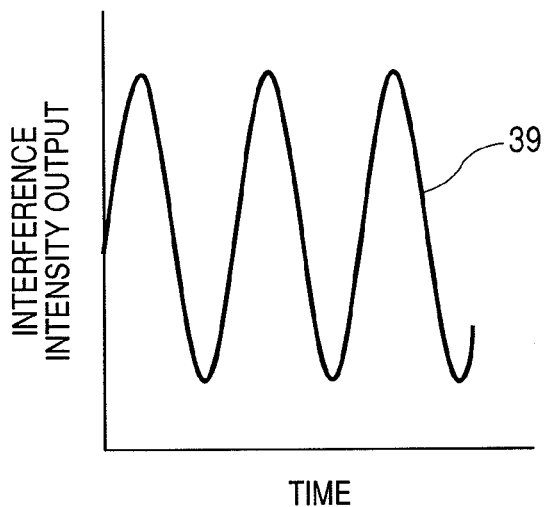

An electrical signal from the photoelectric conversion sensor 18 is processed by a signal processing unit 19 (including an A/D conversion circuit). An output aspect of the photoelectric conversion sensor 18 will be explained below. An embodiment of an output of the photoelectric conversion sensor 18 is shown in FIG. 4. The horizontal axis indicates time and the vertical axis indicates the output 39 of interference intensity as the electrical signal obtained from the photoelectric conversion sensor 18. The laser beam from diode laser 1 is branched into two, and laser beams from acousto-optic modulators (AOMs) 5 and 10 are modulated to slightly different frequencies fa and fb, respectively. If these frequencies fa and fb are respectively set to, for example, 140 MHz and 130 MHz using the acoustic element drive circuit (A) 6 and the acoustic element drive circuit (B) 11, the laser light (beam) combined by the PBS (B) 15 becomes a 10 MHz interference signal (with a period of 100 ns).

As shown in FIG. 4, the photoelectric conversion sensor 18 outputs a 10 MHz interference signal 39. For an output from the signal processing unit 19 (including an A/D conversion circuit), interference intensity, period, and other information are judged (determined) by a judgment circuit 20 and then inputted to a computer 21. Based on a result by the judgment circuit 20, the computer 21 gives instructions to the drive system 9 of the optical path length varying element (optical path length adjustment plate) (A) 8 and the drive system 14 of the optical path length varying element (optical path length adjustment plate) (B) 13.

The configuration of the present invention is characterized by the details of the embodiment explained above.

Then, the modulated laser beam is branched into two by a PBS (C) 23 which is a second branch optical element that comprises same optical element as a second combination optical element. The transmitted P-polarized light is converted to a circularly polarized light by a $\lambda/4$ plate 24 and then imaged to a reference mirror (a reference reflecting plate) 26 by an objective lens 25. The reflected light from the reflective mirror 26 penetrates again through the objective lens 25, is converted to an S-polarized light by the $\lambda/4$ plate 24, and reflected by the PBS (C) 23. On the other hand, the S-polarized light is reflected by the PBS (C) 23, converted to a circularly polarized light by a $\lambda/4$ plate 27, and imaged to a specimen 29 under inspection, such as a disk substrate, by an objective lens 28. The specimen 29 is placed on a table 40 which can rotate and move at least in one axial direction perpendicular to a rotating shaft. The laser beam which penetrated through an objective lens is imaged on the specimen 29 which is under inspection and which is moving in one axial direction while being rotated by the table 40. A total control computer 35 makes it possible to control the rotational direction of the table 40, control the table 40 in one axial direction, and perform positional measurement. The reflected light from the specimen 29 under inspection penetrates again through the objective lens 28, is converted to P-polarized light by the $\lambda/4$ plate 27, and penetrates through the PBS (C) 23. The optical path length from the PBS (C) 23 to the reference mirror 26 and the optical path length from the PBS (C) 23 to the specimen 29 under inspection are set to almost the same distance.

The laser beams reflected by the reference mirror 26 and the specimen 29 under inspection are reflected by the mirror 30 and then imaged on a light-sensitive element (photoelectric conversion sensor) 33 by an imaging lens 31. Since this laser beam contains S-polarized light and P-polarized light, interference does not take place if no measures are taken. Therefore, a polarizing plate 32 is arranged in the optical path with an inclination of 45 degrees to allow interference in the light-sensitive element 33 to take place. An output from the light-sensitive element 33 is processed for an interference signal by a signal processing circuit (phase detector circuit) 34, and a processing result of the interference signal is inputted to the total control computer 35. Specifically, the signal processing circuit (phase detector circuit) 34 compares the interference signal obtained from the light-sensitive element 33 with that for a flat specimen to detect a phase difference $((2\pi/\lambda)\times 2)$, and inputs the phase difference to the total control computer 35, allowing the total control computer 35 to measure the surface shape of the specimen 29 under inspection.

A display device 36 can display a detection result of the specimen 29, and an input device 37 enables input to the total control computer 35. A register device 38 enables input and output of an inspection result to/from the total control computer 35. Furthermore, when manufacturing a disk substrate, for example, arrangements are made so that the display device 36 displays the shape of defect existing on the surface of the disk substrate.

Figure 5A:
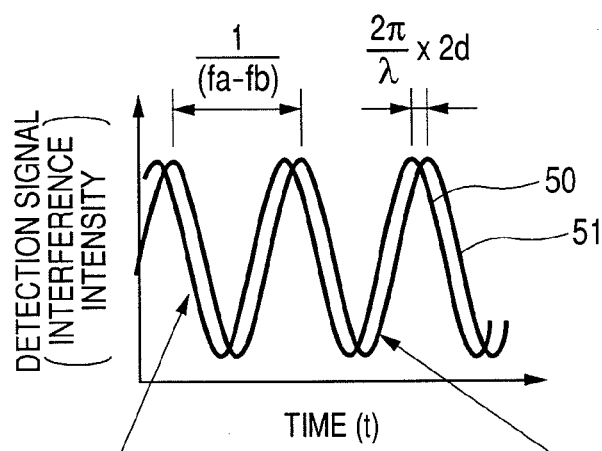
FIG. 5A is a diagram showing temporal variation of a signal obtained by detecting reflected light according to a surface condition of a specimen.
Figure 5B:
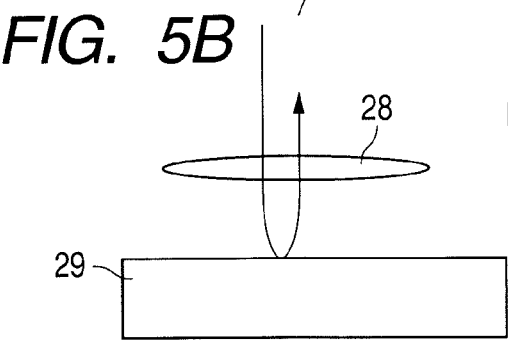
FIG. 5B is a diagram showing a section of a specimen having a flat surface, incidence light, and reflected light.
Figure 5C:
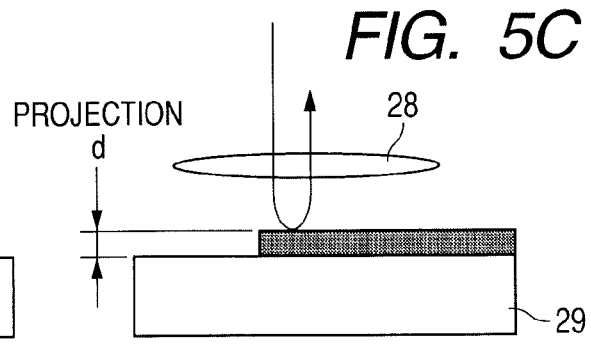
FIG. 5C is a diagram showing a section of a specimen having an uneven surface, incidence light, and reflected light.

An output of the light-sensitive element 33 when there is a projection or level difference on the specimen 29 under inspection, such as a disk substrate, will be described below with reference to FIG. 5. When the specimen 29 is flat as shows in FIG. 5B, the signal becomes a waveform 50 in FIG. 5A. The horizontal axis indicates time and the vertical axis the interference signal. Since the distance between the reference mirror 26 and the specimen 29 remains unchanged, the signal becomes the waveform 50 having a period of 1/(fa−fb), where (fa−fb) is a difference between frequencies fa and fb which are modulated by acousto-optic modulators 5 and 10, respectively. Here, if the specimen 29 has a level difference d as shown in FIG. 5C, the optical path applied to and reflected from the specimen 29 results in a variation of optical path length. The variation is twice the level difference d. Since the reference mirror 26 is fixed, the variation of optical path length changes and therefore the signal becomes a waveform 51, which causes a phase difference $((2\pi/\lambda)\times 2d)$ in comparison with the case of a flat specimen. The surface shape d of the specimen 29 under inspection can be measured by detecting this phase difference $((2\pi/\lambda)\times 2d)$ using the signal processing circuit (phase detector circuit) 34, where $\lambda$ indicates a wavelength of the laser beam emitted by the diode laser light source 1.

Operations with the above configuration will be described below. Effects of the optical path length adjustment plates 8 and 13 on the optical path length and the optical axis are illustrated in FIG. 6. FIG. 6A shows the state before adjustment; FIG. 6B, adjustment in the rotational direction; and FIG. 6C, adjustment in the turn direction. In each of FIGS. 6A to 6C, the top is a plan view and the bottom a front view. The optical path length adjustment plates 8 and 13 have a thickness T. As shown in FIG. 6B, the optical path length adjustment plates 8 and 13 are inclined by θ degrees in the rotational direction 62 by the rotary mechanism 100, with respect to the optical axis. When the optical path length adjustment plates 8 and 13 are thus inclined, the laser beam is refracted within the optical path length adjustment plates 8 and 13. A transmission distance within them becomes T' from the relationship of formula (1) shown below, which causes an optical path difference of (T'−T).

$$\text{Optical path length } T' = T/\cos\theta \quad (1)$$

Furthermore, when the optical path length adjustment plates 8 and 13 are inclined by φ degrees in the turn direction 63 by the turn mechanism 101, the transmission distance within the optical path length adjustment plates 8 and 13 similarly changes to become T" from the relationship of formula (1), which then causes an optical path difference of (T"−T).

By the way, as mentioned above, the coherence length of wide-band diode laser is several millimeters, and the interference intensity is changed even by such an optical path difference. An example output of the photoelectric conversion sensor 18 is shown in FIG. 7. In FIG. 7, the interference intensity at the start of adjustment is 102 and that at the end of adjustment is 103.

Figure 8:
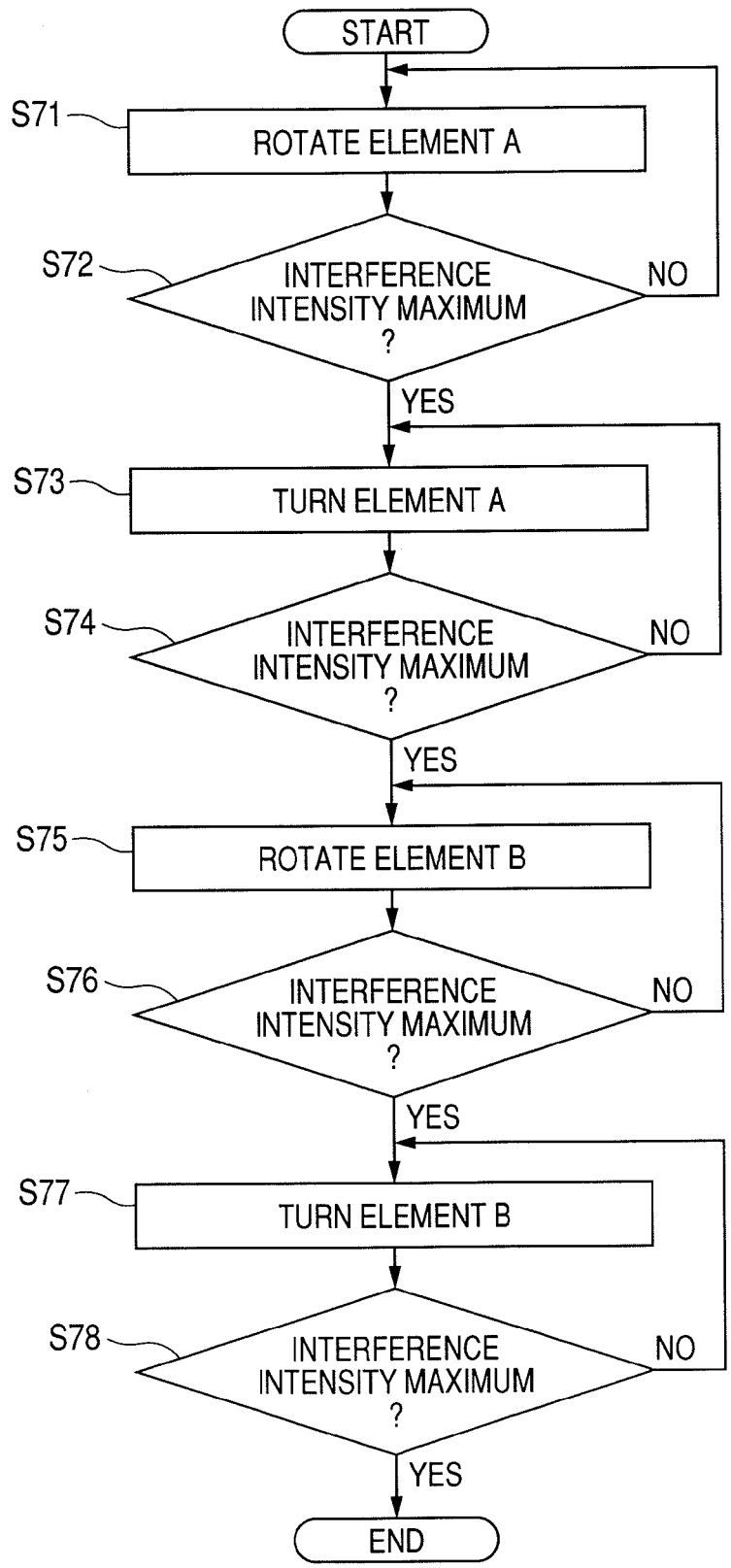
FIG. 8 is a flow chart showing an embodiment of a method for adjusting an optical path length through adjustment of an optical path length varying element (optical path length adjustment plate).

A flow chart for adjustment of the optical path length adjustment plates 8 and 13 is shown in FIG. 8. First, the output of the photoelectric conversion sensor 18 is monitored while rotating the optical path length adjustment plate (A) 8 at a rotational angle of θ in the rotational direction 62 (while changing the optical path length in the rotational direction 62) using the drive system 9 (S71), and the drive system 9 of the optical path length adjustment plate (A) 8 is stopped at a position where the interference intensity is maximized (S72).

Then, the output of the photoelectric conversion sensor 18 is monitored while moving the optical path length adjustment plate (A) 8 at a turn angle of φ in the turn direction 63 (while changing the optical path length in the turn direction 63) using the drive system 9 (S73), and the drive system 9 of the optical path length adjustment plate (A) 8 is stopped at a position where the interference intensity is maximized (S74). This completes adjustment of the optical path length adjustment plate (A) 8.

Likewise, the output of the photoelectric conversion sensor 18 is monitored while rotating the optical path length adjustment plate (B) 13 at a rotational angle of θ in the rotational direction 62 (while changing the optical path length in the rotational direction 62) using the drive system 14 (S75), and the drive system 14 of the optical path length adjustment plate (B) 13 is stopped at a position where the interference intensity is maximized (S76).

Then, the output of the photoelectric conversion sensor 18 is monitored while moving the optical path length adjustment plate (B) 13 at a turn angle of φ in the turn direction 63 (while changing the optical path length in the turn direction 63) using the drive system 14 (S77), and the drive system 14 of the optical path length adjustment plate (B) 13 is stopped at a position where the interference intensity is maximized (S78).

This completes adjustment of the optical path length adjustment plates (A) 8 and (B) 13. The waveform after adjustment becomes 103 as shown in FIG. 7 and the amplitude of interference increases, making it possible to measure the shape of minute concavo-convex defect with high precision based on a phase difference $((2\pi/\lambda) \times 2d)$ by interference according to a projection d, as shown in FIG. 4. Specifically, it becomes possible to measure (and calculate) the height and depth of the measurement surface with high precision based on a phase difference $((2\pi/\lambda) \times 2d)$ by interference.

Anyway, when wide-band diode laser with a short coherence length (of several millimeters) is used for a surface inspection apparatus having the interference phase detection scheme (a surface inspection apparatus which branches a laser beam, modulates the branch laser beams on different frequencies, and measures the surface shape by causing interference of reflected lights on reference and measurement surfaces), it is necessary to arrange acousto-optic modulators (A) 5 and (B) 10 which are modulation optical elements and optical path length varying optical elements (A) 8 and (B) 13 for varying the optical path length in each of the optical paths between the branching optical element PBS (A) 4 and the combining optical element PBS (B) 15 and increase the coherency by adjusting the optical path length varying optical elements (A) 8 and (B) 13.

During inspection, an interference intensity signal shown in FIG. 7 is constantly monitored through signal processing by the signal processing unit 19 based on an electrical signal from the photoelectric conversion sensor 18; and interference intensity, period, and other information are judged by the judgment circuit 20. If the judgment circuit judges that the signal has changed to a predetermined interference intensity or lower, it is preferable that the computer 21 activates each of the drive systems 9 and 14 according to the above-mentioned flow chart and adjusts each of the optical path length varying optical elements (rotation and/or turn of the optical path length adjustment plates) (A) 8 and (B) 13 to correct each optical path length. In this case, if the signal reaches the predetermined interference intensity at one optical path length varying optical element (one optical path length adjustment plate), it is preferable to stop adjustment and continue inspection.

It should be noted that although the optical path length adjustment plates 8 and 13 are described as plane parallel plates, similar effects can be obtained by using wedged glass plates as the optical path length adjustment plates 8 and 13.

FIG. 10 is a diagram showing the configuration in the case of using wedged glass plates. Wedged optical path length adjustment plates 8a and 13a are fixed to the rotary mechanism 100 allowing movement in the rotary direction 62. The rotary mechanism 100 is fixed to the translatory moving portion 104 allowing movement in a translatory direction. The rotary mechanism 100 and the translatory moving portion 104 can be controlled by the drive system 9. The wedged optical path length adjustment plates 8a and 13a are glass plates having a front edge with a thickness t1 and an end edge with a thickness t2. In FIG. 11, effects on the optical path length and optical axis, which are obtained by the wedged optical path length adjustment plates 8a and 13a, are described. FIG. 11A shows the state before adjustment; FIG. 11B, adjustment when changing the optical path length; and FIG. 11C, adjustment in a turn direction. That is, as shown FIGS. 11A and 11B, the wedged optical path length adjustment plates 8a and 13a are moved by the translatory moving portion 104 so as to obtain different widths of the optical paths in the optical path length adjustment plates 8a and 13a. This results in a difference (T2−T1) of the optical paths. In addition, for example, the wedged optical path length adjustment plates 8a and 13a rotate in a direction of θ by the rotary mechanism 100 so that the optical axis is shifted by the distance W while maintaining the difference of the optical paths. According to the flow chart shown in FIG. 8, the rotations in steps S71, S75 may be replaced with translatory movement by use of the translatory moving portion 104 so that the interference intensity is the maximum. Although the thicknesses of the wedged optical path length adjustment plates 8a and 13a are variable in one direction, they may each be trapezoidal having the front edge with the thickness t1 and the end edge with a thickness t3, which obtains similar effects. In this case, the change in the optical path length is twice that of the wedged optical path length varying elements when movement distance of the translatory moving portion is the same.

Second Embodiment

Figure 13:
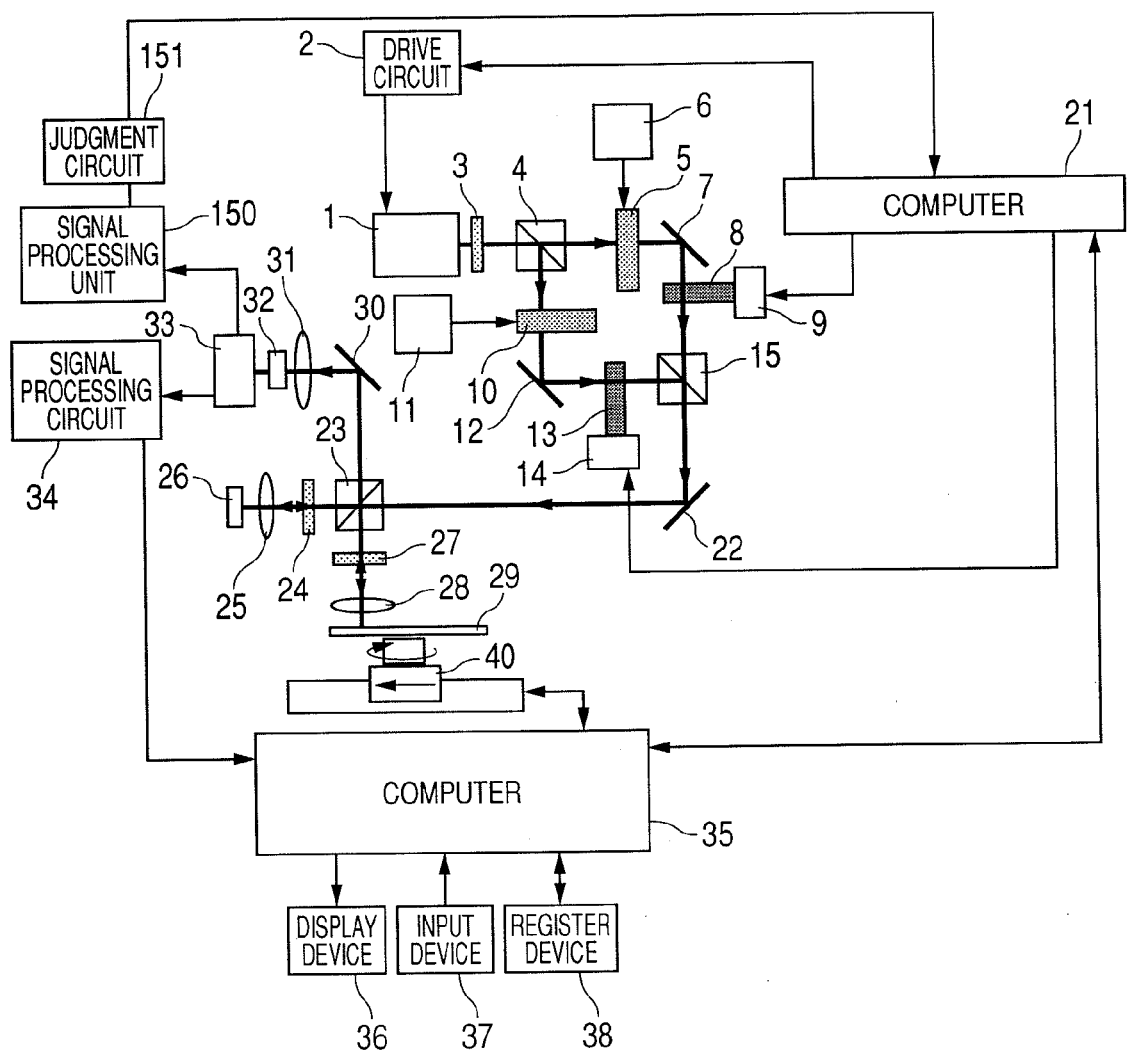
FIG. 13 is a front view showing an outline configuration of a surface inspection apparatus according to another embodiment of the present invention.

A second embodiment of a surface inspection apparatus of the present invention will be described below with reference to FIG. 13. The second embodiment differs from the first embodiment in that the interference intensity is monitored by the light-sensitive element (the sensor) 33 during inspection. Since at least an interference intensity signal 50 for a flat specimen is also detected by the light-sensitive element 33 as shown in FIG. 5, the interference intensity is measured by the signal processing unit 150 (19); and interference intensity, period, and other information are judged by the judgment circuit 151 (20) and then inputted to the computer 21. If the judgment circuit 151 (20) judges (determines) that the signal has changed to a predetermined interference intensity or lower, it is preferable that the computer 21 activates each of the drive systems 9 and 14 according to the above-mentioned flow chart and adjusts each of the optical path length varying optical elements (rotation and/or turn of the optical path length adjustment plates) (A) 8 and (B) 13 to correct each optical path length. In this case, if the signal reaches the predetermined interference intensity at one optical path length varying optical element (one optical path length adjustment plate), it is preferable to stop adjustment and continue inspection. In this manner, the same effect can also be obtained by detecting an interference intensity between the reference surface and the measurement surface using the light-sensitive element 33, and making adjustment based on the flow chart shown in FIG. 8.

Although the above-mentioned first and second embodiments use a polarization beam splitter (PBS) for branching laser beam, the same effect can also be obtained by using an ordinary beam splitter. In this case, the λ/2 plate and the λ/4 plate are not necessary.

Furthermore, although the first and second embodiments have been explained using a disk substrate or the like as a measurement target, it goes without saying that the same effect is also obtained in surface inspection of a mask, a reticle, or a semiconductor wafer used for semiconductors.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An apparatus for inspecting a surface of a specimen, the apparatus comprising:
a laser light source which emits a laser beam having a certain spectrum width;
a modulation system including a first branch optical element which branches an optical path of the laser beam emitted from the laser light source into two, each of frequency modulation elements which modulates each of two laser beams branched by the first branch optical element with mutually different frequencies, each of optical path length adjustment elements which adjusts respective optical path lengths of the each of the two laser beams branched by the first branch optical element, and a first combination optical element which combines laser beams which are modulated with the mutually different frequencies by the each of the frequency modulation elements and whose the each of the optical path lengths is adjusted by the each of the optical path length adjustment elements;
a laser irradiation optical system including a second branch optical element which branches a laser beam that has been combined and output by the modulation system, an specimen light irradiation optics which irradiates a specimen with one laser beam branched by the second branch optical element, a reflecting plate, and a reference light irradiation optics which irradiates the reflecting plate with other laser beam branched by the second branch optical element;
a laser detection optical system including a sensor element which receives a specimen laser beam reflected from the specimen irradiated with the one laser beam by the laser irradiation optical system and a reference laser beam reflected from the reflecting plate irradiated with the other laser beam by the laser irradiation optical system which are combined into a beam by passing through the second branch optical element; and
a signal processor which processes a signal obtained by detecting the combined laser beam in the sensor element of the laser detection optical system so as to obtain information on a surface condition of the specimen,
wherein each of the optical path length adjustment elements includes an optical path length adjustment plate configured to adjust the respective optical path length of the two branched laser beams emitted from the first branch optical element so as to maximize the interference intensity of at least one of the output from the first combination optical element and the laser beams detected by the sensor element.

2. The apparatus for inspecting a surface of a specimen according to claim 1, wherein the laser light source has a spectrum width of several nanometers.

3. The apparatus for inspecting a surface of a specimen according to claim 2, wherein the laser light source is a wide-band diode laser light source having a spectrum width of several nanometers.

4. The apparatus for inspecting a surface of a specimen according to claim 1, further comprising a monitoring unit which monitors an interference condition of the laser beam which is modulated with mutually different frequencies by each of the frequency modulation elements and of which respective optical path lengths is adjusted by each of the optical path length adjustment elements and which is combined with the first combination optical element in the modulation system.

5. The apparatus for inspecting a surface of a specimen according to claim 1, wherein the sensor element of the laser detection optical system detects an interference intensity of the combined laser beam as an interference signal, and the signal processor detects a phase difference of the interference signal based on the interference signal detected by the sensor element of the laser detection optical system so as to obtain the information on the surface condition of the specimen by using information on the phase difference of the detected interference signal.

6. The apparatus for inspecting a surface of a specimen according to claim 1, wherein the signal processor processes the signal detected by the sensor element of the laser detection optical system so as to measure shape of concavo-convex defect on the surface of the specimen.

7. The apparatus for inspecting a surface of a specimen according to claim 1, further comprising a table unit which mounts a specimen so as to be able to rotate and move at least in one direction.

8. A method for inspecting a surface of a specimen, the method comprising the steps of:
- a first branching step of branching an optical path of a laser beam emitted from a laser light source into two;
- modulating the two branched laser beams into two laser beams having mutually different frequencies;
- adjusting respective optical path lengths by passing the two branched laser beams through optical path length adjustment elements;
- a first combining step of combining the two branched laser beams having mutually different frequencies and having their optical path lengths adjusted;
- a second branching step of branching the combined laser beam into two;
- irradiating a specimen with one branched laser beam;
- irradiating a reflecting plate with other branched laser beam;
- a second combining step of combining a laser beam reflected from the specimen irradiated with the one laser beam with a laser beam reflected from the reflecting plate irradiated with the other laser beam;
- detecting the thus combined laser beam; and
- processing a signal obtained by the detecting step so as to obtain information on a surface condition of the specimen,
    - wherein in the step of adjusting respective optical path lengths, at least one of the optical path lengths is adjusted by the interference intensity of the laser beam combined by the first or second combining step; and
    - wherein each of the optical path length adjustment elements includes an optical path length adjustment plate configured to adjust the respective optical path length of the two branched laser beams emitted from the first branching step so as to maximize the interference intensity of at least one of the output from the first combining step and the laser beam detected in the detecting step.

9. The method for inspecting a surface of a specimen according to claim 8, wherein a laser beam emitted from the laser light source has a spectrum width of several nanometers.

10. The method for inspecting a surface of a specimen according to claim 8, further comprising a step of monitoring an interference condition of the combined laser beam which is modulated with the mutually different frequencies and of which the respective optical path lengths is adjusted.

11. The method for inspecting a surface of a specimen according to claim 10, wherein the adjusting step adjusts the respective optical path lengths of the two branched laser beams so as to maximize the interference intensity of the combined laser beam monitored in the monitoring step.

12. The method for inspecting a surface of a specimen according to claim 8, wherein the detecting step detects an interference intensity of the combined laser beam as an interference signal, and wherein the processing step detects a phase difference of the interference signal based on the interference signal detected in the detecting step so as to obtain the information on the surface condition of the specimen by using information on the phase difference of the detected interference signal.

13. The method for inspecting a surface of a specimen according to claim 8, wherein the processing step processes the signal detected in the detecting step so as to measure shape of concavo-convex defect on the surface of the specimen.

14. The method for inspecting a surface of a specimen according to claim 8, wherein the specimen rotates and moves at least in one direction in the irradiating steps.

15. A method for inspecting a surface of a specimen, comprising the steps of:
- a first branching of an optical path of a laser beam emitted from a laser light source into two optical paths;
- modulating the branched laser beams into laser beams having mutually different frequencies; and
    - combining the modulated laser beams into a combined laser beam, after respective lengths of the branched optical paths have been adjusted by using optical path length adjustment elements;
- another branching, this time of the combined laser beam;
- irradiating a specimen rotationally moving in one direction with one laser beam, and irradiating a fixed reflecting plate with other laser beam;
- recombining a laser beam reflected from the specimen rotationally moving in one direction with a laser beam reflected from the fixed reflecting plate irradiated with the other laser beam, the specimen being irradiated with the one laser beam;
- detecting the recombined laser beams by using a sensor; and
- processing a signal obtained by the detection of the sensor so as to obtain information on a surface condition of the specimen;
    - wherein in the step of modulating, at least one of the branched optical path lengths is adjusted based on the interference intensity of the laser combined by the combining or the recombining; and
    - wherein each of the optical path length adjustment elements includes an optical path length adjustment plate configured to adjust the respective optical path length of the two branched optical paths emitted from the first branching, so as to maximize the interference intensity of at least one of the combined laser beam and the recombined laser beams detected by the sensor.

16. The method for inspecting a surface of a specimen according to claim 15, wherein a laser beam emitted from the laser light source has a spectrum width of several nanometers.

17. The method for inspecting a surface of a specimen according to claim 15, wherein the detecting step detects an interference intensity of the recombined laser beam as an interference signal by using the sensor, and wherein the processing step detects a phase difference of the interference signal based on the interference signal detected in the detecting step so as to obtain the information on the surface condition of the specimen by using the information on the phase difference of the detected interference signal.

18. The method for inspecting a surface of a specimen according to claim 15, wherein the processing step processes the signal detected in the detecting step so as to measure shape of concavo-convex defect on the surface of the specimen.

* * * * *